United States Patent [19]

Nelson et al.

[11] Patent Number: 5,232,838
[45] Date of Patent: Aug. 3, 1993

[54] CULTURE MEDIA DEVICE AND METHOD OF USE

[75] Inventors: Robert L. Nelson, Bloomington; Michael D. Crandall, Woodbury; Mary S. Ramos, Minneapolis, all of Minn.

[73] Assignee: Minnesota Mining and Manufacturing Company, St. Paul, Minn.

[21] Appl. No.: 804,295

[22] Filed: Dec. 9, 1991

[51] Int. Cl.⁵ .......................... C12Q 1/24; C12M 1/34
[52] U.S. Cl. ...................................... 435/30; 435/32; 435/34; 435/39; 435/291; 435/299; 435/313; 435/810
[58] Field of Search ............... 435/287, 291, 299, 310, 435/311, 313, 810, 29, 32, 30, 292, 31, 34, 39, 805; 524/157, 548, 555; 424/443–449, 484, 486, 487

[56] References Cited

U.S. PATENT DOCUMENTS

| | | | |
|---|---|---|---|
| 3,769,071 | 10/1973 | Trancik | 424/448 |
| 4,310,509 | 1/1982 | Berglund et al. | 424/448 |
| 4,323,557 | 4/1982 | Rosso et al. | 424/448 |
| 4,539,256 | 9/1985 | Shipman | 428/315.5 |
| 4,565,783 | 1/1986 | Hansen et al. | 435/299 |
| 4,717,667 | 1/1988 | Provonchee | 435/30 |
| 4,898,920 | 2/1990 | Lee et al. | 424/448 |
| 5,089,413 | 2/1992 | Nelson et al. | 435/254 |

FOREIGN PATENT DOCUMENTS

| | | |
|---|---|---|
| 0037150 | 10/1981 | European Pat. Off. |
| 0374905 | 12/1989 | European Pat. Off. |
| 2055741 | 11/1970 | Fed. Rep. of Germany |
| 63-305873A | 12/1988 | Japan |

*Primary Examiner*—Michael G. Wityshyn
*Assistant Examiner*—William H. Beisner
*Attorney, Agent, or Firm*—Gary L. Griswold; Walter N. Kirn; Thomas E. Jurgensen

[57] ABSTRACT

A culture media device comprised of a body member including self-supporting substrate, and coated on its upper surface with a layer of water-based adhesive composition and a layer of a cold-water-soluble powder, is provided. The culture media device can also include an optional cover sheet, covering at least a portion of the body member, and an air-permeable membrane affixed to the upper surface of the substrate to allow for the growth of aerobic microorganisms. In addition, processes of making and using the culture media device are disclosed.

36 Claims, 1 Drawing Sheet

CULTURE MEDIA DEVICE AND METHOD OF USE

FIELD OF THE INVENTION

This invention relates to culture media devices for growing microorganisms. In particular, the present invention relates to culture media devices utilizing various agents, such as nutrient and selective agents, and a dry-powdered gelling agent. Application of an aqueous test sample to the dry-powdered gelling agent forms a reconstituted medium capable of containing and growing microorganisms for quantitative determination.

BACKGROUND OF THE INVENTION

For many years, agar-filled pour plates provided the best method of determining the number of microorganisms in a liquid sample, such as water or milk. However, the use of agar medium is particularly inconvenient and time-consuming. For example, agar medium must be sterilized, melted, and cooled prior to addition of the liquid sample. Furthermore, the sample and medium must be mixed, solidified, and incubated prior to counting of the number of microorganism colonies which grow on the plate.

To date, the prior art has provided several devices useful for assaying liquid specimens for microorganisms which are easier and quicker to use than traditional agar pour-plate technology. For example, German patent application No. 2055741, published May 19, 1971, discloses a microbiological growth medium comprised of an inert card or strip coated or impregnated with a dry-gelled nutritive medium. In one embodiment, the inert card or strip may include optional side walls to prevent shifting of the medium after wetting with a liquid sample. In addition, the nutritive medium may include an adhesive component or be adhered to the card or strip by an intervening adhesive layer. Furthermore, an optional sponge material can be disposed between the card or strip and the nutritive medium, and the nutritive medium can be covered by a semi-permeable membrane.

U.S. Pat. No. 4,565,783 (assigned to the Assignee of the present invention) provides a culture media device comprised of a dry-powdered gelling agent and/or nutrient composition adhered to a waterproof substrate by a layer of water-insoluble adhesive which is non-inhibitory to the growth of microorganisms. Upon application of a liquid sample to the device, the gelling agent(s) hydrates to form a gelatinous medium useful for growing microorganisms contained in the liquid sample. In addition, the device can also include a transparent cover sheet and/or a hydrophobic spacer element with side walls to maintain a pre-determined amount of a liquid sample in contact with the dry-powdered gelling agent(s) and/or nutrient composition of the culture media device. Any nutritive components and/or other agents are incorporated along with the gelling agent(s) into the dry-powdered media coating the device. Alternatively, the nutritive component and/or other agents can be incorporated into a substantially water-free, non-adhesive composition coated onto the waterproof substrate. However, dry-powdered gelling agents cannot be utilized to coat such an embodiment. Commercial embodiments of such devices include Petrifilm TM brand growth media, available from 3M, St. Paul, Minn.

European patent application No. 0374905, published Jun. 27, 1990, also discloses a device for culturing microorganisms comprised of a base sheet composed of a lower water repellent sheet and an upper hydrophilic sheet, such as filter paper. A gel agent or gelatinizer is dispersed in the upper hydrophilic sheet and then solidified. Thereafter, a water-repellent sheet is applied to cover the upper surface of the hydrophilic upper sheet.

U.S. Pat. application Ser. No. 07/354,627, allowed on Sep. 16, 1991, now U.S. Pat. No. 5,089,413, and assigned to the Assignee of the present invention, provides yet another microbiological dry culture medium device. The device is constructed in an analogous fashion to the culture media device of U.S. Pat. No. 4,565,783, described above, except that the base of the device is comprised of an air-permeable membrane adhered to the upper surface of the waterproof substrate. Utilization of the air-permeable membrane provides a means for growing oxygen dependent microorganisms, such as molds, even when an air-impermeable cover sheet is placed over the inoculated culture medium.

The above-described devices have not addressed several areas that are important to the successful construction and use of culture media devices. For example, many conventional adhesives inhibit microorganism growth due to their strongly anionic or cationic nature, or through the deliberate incorporation of anti-microbial agents. Thus, culture devices that incorporate such an adhesive component in, or adjacent to, the nutritive medium may inhibit rather than facilitate the growth of microorganisms.

Even when non-inhibitory adhesives are utilized, such as in U.S. Pat. No. 4,565,783, the water-insoluble nature of the adhesive renders them essentially incapable of holding all but the smallest quantities of water-soluble nutrients and/or other hydrophilic agents. Thus, these nutrients and/or other agents must be incorporated into other 20 water-soluble layers, such as the substantially water-free, cold-water-reconstitutable material of U.S. Pat. No. 4,565,783, and/or various other dry-powdered media. However, these forms of media typically may not provide for adequate control on the release rates of the nutrients and/or other agents. Furthermore, concentration gradients of these components also can occur when these dry media are hydrated.

The lack of control of release rates and creation of concentration gradients is of particular concern with inhibitory agents. Rapid and high dosage release of inhibitory agents may in fact lead to non-selective inhibition of microorganism growth. In addition, creation of concentration gradients of such inhibitory agents may lead to growth inhibition on one portion of the device, but not on another. Under either scenario, the ability to grow and accurately quantify microorganism colony growth is lost.

Finally, utilization of water-absorbing elements, such as sponges and/or filter paper, may not sufficiently contain colony growth, thereby limiting the quantitative value of such devices, and making microorganism colony isolation impractical. In addition, neither of these structures are sufficiently transparent to allow for the counting of colonies through the substrate, thereby also rendering the accurate counting of microorganism colonies nearly impossible.

SUMMARY OF THE INVENTION

The present invention overcomes the deficiencies of the previously described devices by providing a culture media device that includes a layer of a water-based adhesive composition coated on a self-supporting substrate. This adhesive composition is non-inhibitory to microorganism growth, can incorporate significant quantities of nutrients and/or other hydrophilic agents therein at substantially uniform concentrations throughout the layer of the adhesive composition, and releases the nutrients and/or other hydrophilic agents contained therein in a gradual, controlled manner. In addition, the use of cold-water-soluble powder, containing at least one gelling agent, adhered to the adhesive layer eliminates the need for side walls, hydrophobic spacer elements, sponges, or filter paper to absorb and contain an aqueous test sample. Instead, the cold-water-soluble powder rapidly hydrates after addition of the aqueous test sample into a reconstituted medium capable of growing microorganisms contained within the aqueous test sample.

Specifically, the present invention provides a culture media device comprising: (a) a body member formed of a self-supporting, substrate with upper and lower surfaces; (b) a layer of water-based adhesive composition comprising a water-insoluble adhesive, a non-inhibitory emulsifying agent, and at least one hydrophilic agent selected from the group consisting of a hydrophilic nutrient for growing microorganisms, hydrophilic selective agents and combinations thereof, coated on the upper surface of the substrate; and (c) a layer of a cold-water-soluble powder, comprising at least one gelling agent, uniformly adhered to the layer of the water-based adhesive composition.

Preferably, the self-supporting substrate is substantially water-proof. In addition, the culture media device according to the present invention can optionally include a cover sheet, such as a transparent film, which is releasably adhered to at least a portion of the body member. The inner surface (i.e., powder facing) of this cover sheet is preferably capable of being coated with a noninhibitory adhesive and a layer of cold-water-soluble powder comprising at least one gelling agent. This additional quantity of cold-water-soluble powder increases the capacity of the culture media device, such that larger volumes of aqueous test samples can be contained and hydrated into the reconstituted medium for growing microorganisms without the need to resort to spacer elements, side walls, sponges, or filter paper.

In another embodiment, the present invention can provide a culture media device capable of growing aerobic microorganisms when an air-impermeable cover sheet is used to cover the reconstituted medium hydrated by an aqueous test sample. Specifically, the body member comprises an air-permeable membrane affixed to the upper surface of the substrate. A layer of the water-based adhesive composition is coated on the top surface of the membrane, and a layer of cold-water-soluble powder is adhered to the layer of the adhesive composition. Utilization of the air-permeable membrane in this culture media device allows a constant source of air to reach the microorganisms growing in the reconstituted medium during incubation of the inoculated culture media device.

In yet another embodiment, the present invention can provide a method of making a culture media device comprising the steps of: (a) providing a body member in the form of a self-supporting substrate having upper and lower surfaces, and a water-based adhesive composition comprising a water-insoluble adhesive, a non-inhibitory emulsifying agent, and at least one hydrophilic agent selected from the group consisting of hydrophilic nutrients for growing microorganisms, and hydrophilic selective agents; (b) coating the water-based adhesive composition on the upper surface of the substrate; and (c) affixing a uniform layer of cold-water-soluble powder, comprising at least one gelling agent to the layer of the water-based adhesive composition.

In yet a further embodiment, the present invention can provide a method of using a culture media device comprising the steps of: (a) providing a culture media device comprising a body member including a self-supporting substrate with upper and lower surfaces, and a layer of water-based adhesive composition coated on the upper surface of the substrate, wherein the water-based adhesive composition comprises a water-insoluble adhesive, a non-inhibitory emulsifying agent, and at least one hydrophilic agent selected from the group consisting of a nutrient for growing microorganisms, a selective agent, and combinations thereof, and wherein a uniform layer of cold-water-soluble powder comprising at least one gelling agent is adhered to the layer of the water-based adhesive composition; (b) inoculating the culture media device with a predetermined volume of an aqueous test sample to form a reconstituted medium; (c) incubating the culture media device for a predetermined period of time; and (d) counting the number of microorganism colonies growing on the reconstituted medium.

These and various other advantages and features of novelty which characterize the invention are pointed out with particularity in the claims annexed hereto and forming a part hereof. However, for a better understanding of the invention, its advantages, and objects obtained by its use, reference should be had to the Drawing which forms a further part hereof, and to the accompanying descriptive matter, in which there is illustrated and described preferred embodiments of the invention.

DEFINITIONS

For the purposes of this invention,

"aqueous test sample" refers to an aqueous medium, including food samples that are homogenized, diluted, or suspended in the aqueous medium, that can contain various microorganisms therein;

"powder" refers to a particulate material (e.g., of one or more gelling agents) wherein the particles have an average diameter suitable for use in the culture media device(s) of the present invention, preferably a diameter of from about 400 $\mu$ to about 10 $\mu$, more preferably a diameter of from about 90 $\mu$ to about 30 $\mu$;

"cold-water-soluble powder" refers to a powder that forms a gel in room temperature water (e.g., from about 18° C. to about 24° C.) when combined with an aqueous test sample;

"non-inhibitory emulsifying agent" refers to an emulsifying agent, preferably a nonionic emulsifying agent, that is suitable to disperse a water-insoluble adhesive in an aqueous medium, and which does not substantially inhibit the growth of the microorganisms intended to be grown;

"reconstituted medium" refers to a solution or gel formed from the reconstitution of a cold-water-soluble powder with water or an aqueous test sample;

"air-permeable" refers to a membrane that, when substantially exposed at its edges to air, is sufficiently permeable to air in the horizontal direction (i.e., parallel to its top and bottom surfaces) to provide an adequate supply of air to an overlying reconstituted medium in order to support the growth of aerobic microorganisms in the reconstituted medium;

"water-insoluble adhesive" refers to a hydrophobic adhesive that is substantially insoluble in an aqueous medium, and which is preferably formed by aqueous emulsion polymerization techniques;

"water-based adhesive composition" refers to an adhesive composition of a water-insoluble adhesive that is dispersed in an aqueous medium by a non-inhibitory emulsifying agent prior to coating onto a substrate;

"substantially impermeable to microorganisms and water vapor" refers to a cover sheet that prevents undesired contamination and hydration of the underlying layers of the water-based adhesive composition and cold-water-soluble powder during shipping, storage, and use of the culture media device(s), and that avoids desiccation of the reconstituted medium, such that the reconstituted medium is suitable to support the growth of microorganisms during an incubation period; and "selective agent" refers to any element, compound, or composition that functions to inhibit the growth, and/or facilitate the identification, of microorganisms grown on the culture media device(s) according to the present invention.

BRIEF DESCRIPTION OF THE DRAWING

The invention may be further illustrated by reference to the accompanying Drawing wherein.

FIG. is a top perspective view, partially in section, of a first embodiment of a culture media device according to the present invention.

DETAILED DESCRIPTION OF EMBODIMENTS OF THE INVENTION

Culture Media Devices

Figure 1:
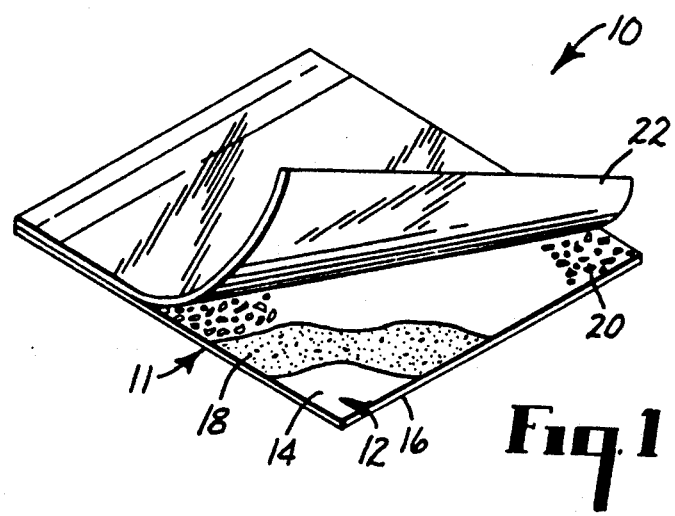

A first embodiment will be described with reference to FIG. 1, which illustrates a culture media device 10 in accordance with the present invention. Culture media device 10 includes body member 11 comprising self-supporting substrate 12 having upper and lower surfaces 14 and 16, respectively. Substrate 12 is coated on its upper surface 14 with a layer of water-based adhesive composition 18. Cold-water-soluble powder, comprising one or more gelling agents, is adhered in a thin, relatively uniform layer 20 to the layer of water-based adhesive composition 18. Once inoculated with an aqueous test sample (not shown), the layer of cold-water-soluble powder 20 quickly hydrates to form a reconstituted medium (not shown), which in turn is capable of containing and growing microorganisms present in the aqueous test sample. In addition, culture media device 10 can optionally include cover sheet 22, to cover and further contain the reconstituted medium after inoculation of culture media device 10 with the aqueous test sample.

Figure 3:
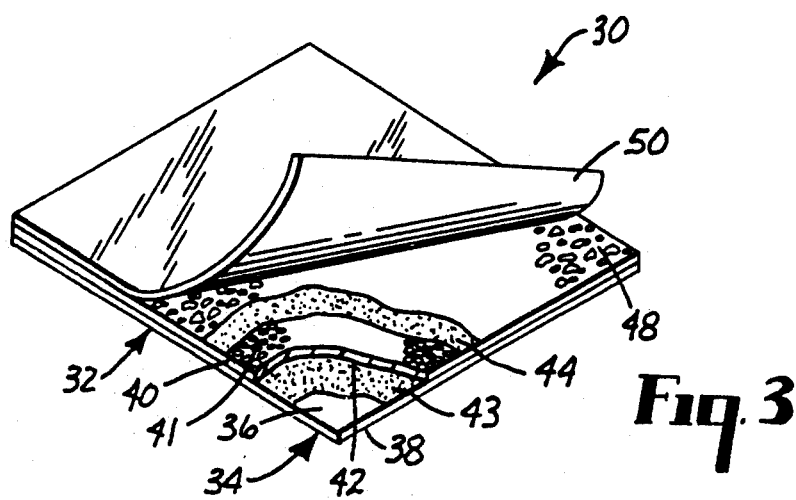
FIG. 3 is a top perspective view, partially in section, of a second embodiment of a culture media device according to the present invention.

In an alternative embodiment illustrated in FIG. 3, culture media device 30 includes a body member 32 comprising self-supporting substrate 34, having upper and lower surfaces 36 and 38, respectively. Air-permeable membrane 40, including top and bottom surfaces 41 and 42, respectively, is affixed to upper surface 36 of substrate 34 by adhesive layer 43. A layer of water-based adhesive composition 44 is shown coated on top surface 41 of air-permeable membrane 40. In a like manner to culture media device 10 illustrated in FIG. 1, cold-water-soluble powder, comprising one or more gelling agents, is shown adhered in a thin, relatively uniform layer 48 to the layer of water-based adhesive composition 44. Furthermore, culture media device 30 can optionally include cover sheet 50.

Figure 2:
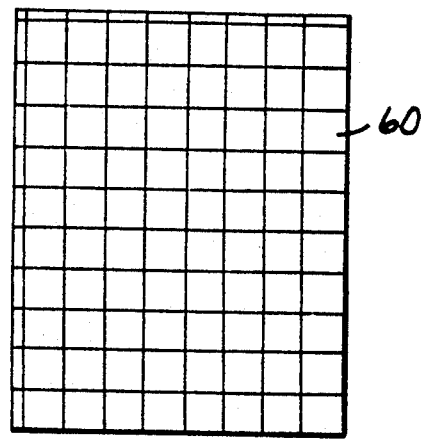
FIG. 2 is a top view of the culture media device of FIG. 1 showing a grid pattern printed on a body member of the culture media device.

When using either of culture media devices 10 or 30 illustrated in FIGS. 1 or 3, an accurate count of the colonies of microorganisms present is often desirable. As illustrated in FIG. 2, the counting of colonies of microorganisms, such as bacteria colonies, can be facilitated by imprinting square grid pattern 60, either on substrate 12 or 34, or on air-permeable membrane 40 of culture media device(s) 10 or 30. In addition, it will also be appreciated that square grid pattern 60 could be imprinted on cover sheets 22 and 50 to aid in the counting of microorganism colonies.

Body Member

In both of culture media devices 10 and 30 illustrated, respectively, in FIGS. 1 and 3, body members 11 and 32 include self-supporting substrates 12 and 34. Substrates 12 and 34 preferably comprise a relatively stiff film of a polymeric material, including without limitation, polyolefins such as polypropylene and polyethylene, polyesters, polystyrenes, or mixtures thereof. Preferably, the self-supporting substrates 12 and 34 are substantially water-proof, such that they will not substantially absorb or otherwise be affected by water. Polyester films approximately $100\mu$ to $180\mu$ thick, polypropylene films approximately $100\ \mu$ to $200\mu$ thick, and polystyrene films approximately $300\mu$ to $380\mu$ thick have been found to work well with the present invention. Other suitable substrates include paper with a polyethylene or other substantially water-proof coating, such as "Schoeller Type MIL" photoprint paper (Schoeller, Inc., of Pulaski, N.Y.). In addition, substrate 12 and 34 can be transparent, translucent, or opaque, depending on whether one wishes to view and count microorganism colonies through substrate 12 and 34.

In addition to self-supporting substrate 34, body member 32 of culture media device 30, illustrated in FIG. 3, includes air-permeable membrane 40 affixed to upper surface 36 of substrate 34. In addition to facilitating the growth of aerobic organisms, air-permeable membrane 40 is also useful in instances where the microorganisms require air for reasons in addition to, or other than for growth, for example, to oxidize a dye that renders the microorganism colonies more easily visible, as discussed more fully below.

Horizontal passage of air for a particular membrane is most conveniently estimated by evaluating the vertical air permeability of the membrane (i.e., permeability in a direction normal to top and bottom surfaces 41 and 42 of membrane 40). Vertical air permeability can be determined by any suitable means. For purposes of the instant specification and claims, vertical air permeability is determined by ASTM-D-726-58, Method A, using a Gurley ™ densitometer to measure the time in seconds needed to pass 50 ml of air through air-permeable membrane 40 (i.e., generally air-permeable membrane 40 itself, absent any layer of water-based adhesive composition 44, cold-water-soluble powder 48, substrate 32, etc.). This permeability is referred to herein as "Gurley Porosity". In this regard, it is preferred that air-permeable membrane 40 have a Gurley Porosity value of less than about 100 seconds, more preferably less than about 50 seconds, and most preferably less than about 25 seconds.

Those skilled in the art will recognize that the optimum thickness of air-permeable membrane 40 will depend in part upon the air and water permeability of membrane 40. In general, a uniform thickness between about $10\mu$ and about $500\mu$ is suitable, a uniform thickness between about $20\mu$ and about $100\mu$ is preferred, and a uniform thickness between about $40\mu$ and about $80\mu$ is particularly preferred.

Suitable materials useful for air-permeable membrane 40 include, but are not limited to, microporous films and microporous non-woven webs of synthetic or natural materials. Such materials are readily available, and methods of preparing them are well known to those skilled in the art. Preferred materials for use in a device of the invention include microporous membranes such as those prepared according to Example 23 of U.S. Pat. No. 4,539,256, the disclosure of which is incorporated herein by reference. These preferred materials can be made of any polymer suitable for use in the method of preparation described in the '256 patent.

Particularly preferred are air-permeable membranes 40 made of polypropylene, polyethylene, polyethylene terephthalate, polybutylene terephthalate, nylon, polyvinylidine fluoride, or copolymers or blends thereof. Examples of preferred air-permeable membranes include Exxaire TM breathable polyolefin film (50 thick; Gurley Porosity about 50 seconds; product number 10-B04; Exxon Chemical Co., Polymers Group); Exxaire TM breathable polyolefin film ($50\mu$ thick; Gurley Porosity about 100 seconds; product number 7-B03; Exxon Chemical Co., Polymers Group); microporous polyethylene film (20 thick; Gurley Porosity about 25 seconds); and 3M Micropore TM tape, which has a non-woven rayon web as backing, and as an adhesive tape, is $125\mu$ thick and has a Gurley Porosity about 0.1 seconds (product number 1530; 3M Company, St. Paul, Minn.).

Water-Based Adhesive Composition

Preferably, the layer of water-based adhesive composition 18 and 44 is sufficiently transparent when wetted by an aqueous test sample to enable the viewing of the colonies of microorganisms through body member 11 and 32 and/or cover sheet 22 and 50 of culture media devices 10 and 30. Water-based adhesive composition layers 18 and 44 which turn milky upon exposure to water are less preferred, but may be used in conjunction with a non-transparent substrate 12 and 34 and/or air-permeable membrane 40, or where colony visualization is not required.

It is preferred that the water-insoluble adhesive of the water-based adhesive composition be a pressure-sensitive adhesive. More preferably, the water-insoluble adhesive is a pressure-sensitive adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 95:5 to 98:2.

In a preferred embodiment, the alkyl acrylate monomer comprises a lower alkyl ($C_2$ to $C_{10}$) monomer of acrylic acid, including, without limitation, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl ($C_2$ to $C_5$))(meth)acrylamides, N-methyl (meth)acrylamide, N,N-dimethyl(meth)acrylamides, or mixtures thereof. Particularly preferred water-insoluble adhesive copolymers in accordance with the present invention include a copolymer of IOA and ACM, or a copolymer of IOA and NVP, both formed in a weight ratio of about 98:2.

The water-insoluble adhesive component of the water-based adhesive composition is preferably formed by aqueous emulsion polymerization. In preparing the water-insoluble adhesive via emulsion polymerization, the above-described alkyl acrylate and alkyl amide monomers and a polymerization initiator are combined according to the preferred weight ratios in an aqueous medium that includes a noninhibitory emulsifier. (See e.g., pending patent application, U.S. Ser. No. 07/804,296, filed Dec. 9, 1991, M. Crandall et al., assigned to the Assignee of the present invention, the disclosure of which is herein incorporated by reference.)

A typical process for producing the emulsified water-based adhesive composition according to the present invention involves first preparing an aqueous solution of a nonionic emulsifier and water. A previously-prepared mixture of the alkyl acrylate and alkyl amide monomers in the desired weight ratios, and a nonionic oleophilic polymerization initiator, is then mixed and dispersed in the aqueous solution via the nonionic emulsifier. The mixing is carried out under homogenization conditions for about one minute in order to prepare an oil-in-water emulsion.

Preferably, the monomers comprise from about 20 to 60 percent by weight, and more preferably about 30 to about 50 percent by weight, of the total weight of the monomers, emulsifier, polymerization initiator, and water combined. In addition, the reaction mixture can optionally contain other additives, including neutral nonionic cross-linking agents, such as 4-acryloyloxy benzophenone or 1,6-hexanediol diacrylate (HDDA), at a level of from about 0.01% to about 0.5%, preferably about 0.02% to about 0.1%, and most preferably about 0.03% to about 0.08% by weight based on the total weight of the monomers present.

The resulting oil-in-water emulsion is heated to induction temperature and stirred under nitrogen until polymerization occurs, as signaled by a reaction exotherm. Stirring is continued, at an elevated temperature (e.g., from about 50° C. to about 90° C.), for about two hours, after which the reaction vessel is cooled to room temperature and the polymeric product is recovered by filtration. If the resulting composition is to be coated directly, any additives such as nutrients and hydrophilic selective agents, are added with stirring. Water is added or removed to reach an appropriate coating viscosity, and the mixture is coated onto an appropriate substrate. Typically, the adhesive particle diameter ranges from about $0.1\mu$ to about $0.9\mu$, and the filtered reaction mixture has a Brookfield viscosity of about 5 to about 15 cps. In addition, appropriate adjustments to the pH of the adhesive composition are made, as needed, to insure that the water-based adhesive composition is non-inhibitory to the growth of microorganisms. Typically, the pH of the water-based adhesive composition should be maintained at a pH of about 5 to about 9, more preferably at a pH of about 6 to about 8.

The non-inhibitory emulsifying agent utilized in the formation of the water-insoluble adhesive, and resulting water-based adhesive composition, is preferably a non-ionic emulsifying agent. Typical nonionic emulsifying agents capable of being used in the present invention are formed by the reaction of ethylene oxide with active hydrogen compounds such as phenols, alcohols, carboxylic acids, amines, and amides. Furthermore, these nonionic emulsifying agents also typically exhibit a hydrophilic-lipophilic balance (HLB) of from about 10 to about 20, preferably from about 12 to about 18.

Suitable nonionic emulsifiers according to the present invention include, without limitation, polyethers, e.g., ethylene oxide and propylene oxide condensates in general, which include straight- and branched $C_2$ and $C_{18}$ alkyl, alkylaryl and alkenyl alcohol based copolymers of ethylene oxide and propylene oxide such as the Tergitol TM X series of emulsifiers (Union Carbide Co.), block copolymers of ethylene oxide and propylene oxide such as Pluronic TM and Tetronic TM emulsifiers (BASF Co.), and Tweens TM and Spans TM nonionic emulsifiers (ICI, Inc.), which denote polyoxyalkylene derivatives of sorbitan and fatty acid esters. Specific examples of nonionic emulsifiers include, but are not limited to, ethoxylated fatty alcohols, ethoxylated alkylphenols, ethoxylated fatty acids, ethoxylated fatty acids, sorbitan derivatives, sucrose esters and derivatives, ethylene oxide-propylene oxide block copolymers, fluorinated alkyl polyoxyethylene ethanols, and mixtures thereof.

A preferred nonionic emulsifying agent according to the present invention is an octyl phenoxy poly(ethylene oxide) ethanol (e.g., IGEPAL TM CA-897; Rhone Poulenc of Princeton, N.J.). Preferably, the nonionic emulsifier is used at a level of about 2% to about 10%, more preferably about 3% to about 5%, and most preferably about 4% by weight, based on the total weight of the monomers, emulsifier and polymerization initiator combined.

Preferably, the polymerization initiator used in the formation of the water-based adhesive composition comprises a nonionic oil-soluble initiator. Non-limiting examples of suitable polymerization initiators include peroxides such as benzoyl peroxide or lauroyl peroxide, as well as azo initiators, such as 2-(carbamoylazo)-isobutyronitrile (e.g., "V-30 initiator"; Wako Chemicals, Dallas, Tex.) or azobisisobutyronitrile ("AIBN initiator"; DuPont Co., Wilmington, Del.). Particularly preferred among these is lauroyl peroxide, used at level of about 0.02% to about 0.3%, more preferably about 0.05% to about 0.25%, and most preferably about 0.07% to about 0.2% by weight, based on the total weight of the monomers.

As noted above, the water-based adhesive composition incorporates one or more hydrophilic agents, including nutrients, selective agents, or combinations thereof. The specific nutrients and/or selective agents used in the water-based adhesive composition will be apparent to those skilled in the art in view of the present specification depending upon the particular organisms to be grown and/or to be selectively dyed or inhibited. After incorporation of the hydrophilic agents, and prior to coating, the pH of the water-based adhesive composition is normalized to about pH 6.5 to about pH 7.5, preferably about pH 7, to help ensure that the water-based adhesive composition does not inhibit the growth of desired microorganisms.

Non-limiting examples of suitable nutrients include meat peptone, casein peptone, beef extract, lactose, glucose, galactose, as well as fats, minerals and vitamins. Specific examples of nutrient formulations suitable for use in the present invention include, without limitation, Violet Red Bile, Standard Methods, and Baird-Parker nutrient formulations (Acumedic, Inc., Baltimore, Md.) (See e.g., Tables 3 and 4 herein).

The hydrophilic selective agents that can be incorporated into the water-based adhesive composition provide a means for selectively inhibiting or identifying microorganisms transferred to culture media devices 10 and 30 from the aqueous test sample. Suitable selective agents can include antibiotics, such as colistin methane sulfonate or nalidixic acid, for inhibition of unwanted organisms. Other suitable inhibitory selective agents include inhibitory salts, such as bile salts which, for example, can be used to selectively grow gram-negative microorganisms (i.e., inhibit the growth of gram-positive microorganisms).

Another useful class of hydrophilic selective agents include dyes that are metabolized by, or otherwise react with, growing microorganisms, and in so doing cause the microbial colonies to be colored or fluoresce for ease of visualization and quantification. Non-limiting examples of such dyes include triphenyl tetrazolium chloride, p-tolyl tetrazolium red, tetrazolium violet, veratryl tetrazolium blue, crystal violet, neutral red, and 5-bromo-4-chloro-3-indolyl phosphate disodium salt. Particularly preferred dyes in accordance with the present invention include crystal violet, neutral red and 5-bromo-4-chloro-3-indolyl phosphate disodium salt. However, it will be appreciated that other suitable dyes can be used depending on the particular organism(s) to be identified.

After formation, the water-based adhesive composition is coated (preferably, knife-coated) onto body member 11 and 32 at a thickness that is preferably less than the diameter of the particles of the cold-water-soluble powder to be adhered to adhesive layer 18 and 44. When coating the water-based adhesive composition, the object is to apply enough adhesive composition to facilitate adherence of the cold-water-soluble powder to upper surface 14 of substrate 12, or upper surface 41 of air-permeable membrane 40, but not so much that the particles comprising the cold-water-soluble powder become completely embedded in the layer of water-based adhesive composition 18 and 44. Generally, a water-based adhesive composition level of from about 0.20 to about 0.001 g/cm², more preferably from about 0.12 to about 0.006 g/cm², and most preferably from about 0.08 to about 0.008 g/cm² is suitable. The layer of water-based adhesive composition 18 and 44 is then preferably dried to remove excess remaining water before coating with the layer of cold-water-soluble powder 20 and 48.

Cold-Water-Soluble Powder

Suitable gelling agents for inclusion in the cold-water-soluble powder include both natural and synthetic gelling agents that form solutions in water at room temperature. Standard gelling agents, such as hydroxyethyl cellulose, carboxymethyl cellulose, polyacrylamide, locust bean gum, guar gum, and algin, as well as super-absorbent materials, including glycol modified polysaccharides, such as Ucargel TM super absorbent agents (Union Carbide, Boundbrook, N.J.), and starch-graft-poly(sodium acrylate-co-acrylamides), such as Water Lock TM super absorbent agents (Grain processing Corp., Muscatine, Iowa), form solutions in water at room temperature, and are suitable gelling agents for providing powders which are "cold-water-soluble."

Preferably, the cold-water-soluble powder is comprised of a mixture of super-absorbent materials exhibiting water absorbency of from about 50 ml/g to about 200 ml/g, more preferably 100 ml/g to about 180 ml/g, and standard gelling agents with water absorbency of from about 1 ml/g to about 20 ml/g, more preferably about 5 ml/g to about 10 ml/g. Use of a mixture of super-absorbent materials and standard gelling agents in the cold-water-soluble powder of the present invention provides a powder coating that can rapidly hydrate to contain a relatively large sample volume (e.g., about 5 ml) on a substrate surface area of a size which is easily handled and stored (e.g., about 75 cm$^2$), while using a relatively small amount of cold-water-soluble power (e.g., only a single layer of powder). In this regard, the cold-water-soluble powder of the present invention preferably comprises Ucargel TM powder and/or Water Lock TM A-100 powder in combination with standard gelling agents, such as locust bean gum and/or xanthum gum. In a particularly preferred embodiment, Ucargel TM powder, Water Lock TM A-100 powder, locust bean gum, and xanthum gum are combined in a 1:1:1:1 weight ratio to provide the cold-water-soluble powder of the present invention.

The gelling agent is included in the cold-water-soluble powder in a sufficient amount so that a predetermined quantity of an aqueous test sample can be applied and maintained on body member 11 and 32 without having any of the aqueous test sample run off the edge of body member 11 and 32. Preferably, sufficient gelling agent is provided so that from about 1 ml to about 5 ml of an aqueous test sample, placed on powder-coated body member 11 and 32, will form a gelatinous reconstituted medium. In this regard, it is particularly preferred that the combination of the cold-water-soluble powder and aqueous test sample form from about a 5% to about a 15% solution, more preferably from about a 7% to about a 12% solution of the mixture. Gels such as these will allow convenient handling and stacking, and provide distinct colony identification. In most cases 2.5 mg to 5 mg of cold-water-soluble powder on a surface area of 1 cm$^2$ will provide a sufficiently viscous gel when hydrated with 1 ml to 5 ml of an aqueous test sample. No mixing is required, and there is no need for a user to heat the medium or otherwise treat it to obtain the gelled reconstituted medium.

Furthermore, the size of the cold-water-soluble powder particles can be used to control the coating weight per unit area. For example, approximately 100 mesh powder coats to a weight of about 50 mg/5 cm diameter disc and a 400 mesh powder coats to a weight of about 25 mg/$^5$ cm diameter disc. If additional amounts of gelling agent are required, optional cover sheet 22 and 50 of culture media devices 10 and 30 can also be coated with cold-water-soluble powder.

In some embodiments, it will also be desirable to incorporate nutrients into the cold-water-soluble powder, along with the gelling agent(s). Inclusion of the nutrients is particularly useful to help facilitate the initial growth of microorganisms transferred to culture media device 10 and 30 through the aqueous test sample. Further, a dye or other reagent can also be included in the cold-water-soluble powder to further enhance the visualization of microorganism colonies.

Cover Sheet

In a preferred embodiment, cover sheet 22 and 50 is affixed to one edge of body member 11 and 32. Cover sheet 22 and 50 is preferably transparent to facilitate counting of the microorganism colonies, and is substantially impermeable to bacteria and water vapor. Generally, cover sheet 22 and 50 will have the same properties, such as transparency and preferred water impermeability, as substrate 12 and 34, but need not be as stiff. Furthermore, cover sheet 22 and 50 can have patterns imprinted thereon, such as square grid pattern 60, or a mask-edge (not shown) to aid in the counting of microorganisms in colonies, to provide a target for placement of the aqueous test sample, and/or for aesthetic reasons.

Cover sheet 22 and 50 can be selected to provide the amount of oxygen transmission necessary for the type of microorganism desired to be grown. For example, polyester films have a low oxygen permeability (less than 0.78 g/100 cm$^2$/24 hours per 25$\mu$ of thickness), and would be suitable for growing anaerobic bacteria, or aerobic bacteria when utilized with air-permeable membrane 40 as a component of body member 32 of culture media device 30. On the other hand, some forms of polyethylene have a relatively high oxygen permeability (approximately 78 g/100 cm$^2$/24 hours per 25$\mu$ of thickness), and would be suitable for the growth of aerobic organisms, with or without the use of an air-permeable membrane 40. The presently preferred material for cover sheet 22 and 50 is a 1.6 mil biaxially-oriented polypropylene film. In addition, cover sheet 22 and 50, can also be coated with optional layers of noninhibitory adhesive and cold-water-soluble powder (not shown). It is understood that cover sheet 22 and 50 can alternatively be affixed to body member 11 and 32, and that it can be free of any coating, or may be coated only with a layer of noninhibitory, pressure-sensitive adhesive.

Although both of the embodiments illustrated in FIGS. 1 and 3 have cover sheet 22 and 50 attached to culture media device 10 and 30, it is also contemplated within the scope of the invention that culture media devices 10 and 30 can be uncovered, and simply placed in a sterile environment during storage and incubation.

The noninhibitory adhesive optionally used on cover sheet 22 and 50 can comprise the preferred water-based adhesive composition of the present invention, or any other suitable, noninhibitory adhesive, including the adhesives disclosed in U.S. Pat. No. 4,565,783, the disclosure of which is herein incorporated by reference. Suitable gelling agents for inclusion in the cold-water-soluble powder coating of cover sheet 22 and 50 (if such are contained in the coating) include the above-described gelling agents, which form a gelatinous reconstituted medium in water at room temperatures.

Advantages of the Invention

Culture media devices 10 and 30 according to the present invention provide several advantages over previously known culture media devices. For example, the water-based adhesive composition of the present invention comprises an aqueous emulsion that allows for the incorporation of significantly greater amounts of hydrophilic agents into the layer of water-based adhesive composition 18 and 44 of culture media devices 10 and 30 than was possible with previously-used solvent-based adhesive compositions. In particular, the hydrophilic agents can comprise from about 2:3, to about 1:10, more preferably from about 1:2 to about 1:4, and most preferably about 1:3 parts by weight of a hydrophilic agent to total parts of the water-based adhesive composition. In contrast, typical solvent-based adhesive compositions used in known culture media plates can incorporate no more than a weight ratio of about one part-by-weight hydrophilic agent to 8000 parts of the solvent-based adhesive composition. For example, in a forty percent (40%) solution of the water-based adhesive composition of the present invention, up to about fifty percent (50%), more preferably from about twenty percent (20%) to about forty percent (40%) by weight, based on the weight of the water-insoluble adhesive, non-inhibitory emulsifying agent, and hydrophilic agent(s) combined, can comprise a standard nutrient composition, such as a Baird-Parker or Violet Red Bile nutrient formulation, whereas virtually none of the same nutrient composition can be incorporated into a solvent-based adhesive composition, such as disclosed in U.S. Pat. No. 4,565,783.

In addition to having increased solubility, the incorporated hydrophilic agents are dispersed in a relatively uniform manner throughout the layer of water-based adhesive composition 18 and 44. Accordingly, these agents will diffuse from this layer at a relatively even rate and at a relatively constant gradient across the surface of the layer of water-based adhesive composition 18 and 44. The control of release rates that is provided by the even dispersion of hydrophilic agents throughout the layer of water-based adhesive composition 18 and 44 can be particularly critical when using selective inhibitory agents. By applying a uniform rate of inhibition throughout the reconstituted medium, a more accurate quantitative measure of the microbial colonies growing in the medium can be obtained. In addition, the slower release of inhibitory agents will help prevent the nonselective toxic effects of a large dosage of inhibitory agent on the microorganisms transferred to the reconstituted medium of the device via the aqueous test sample.

The ability to incorporate substantial quantities of hydrophilic agents into the layer of water-based adhesive composition 18 and 44 also provides advantages in the construction and usage of culture media devices 10 and 30 according to the present invention. For example, many desirable selective agents typically could not be used with previous culture media devices. In particular, heavy-metal salts and antibiotic selective agents should not be incorporated into culture media devices or otherwise handled without the use of appropriate safety equipment, such as respirators, gloves, or other protective equipment. This is especially true when such agents comprise a component of powders or other dry particulates used in a culture media device. However, such concerns are substantially eliminated or reduced by incorporating these potentially hazardous selective agents into the layer of water-based adhesive composition 18 and 44 of culture media devices 10 and 30 according to the present invention. In particular, incorporating such agents into the layer of water-based adhesive composition 18 and 44 should substantially prevent these agents from dispersing in the air, thereby preventing a contamination risk to the users of culture media devices 10 and 30.

Furthermore, incorporation of the hydrophilic agents into the layer of water-based adhesive composition 18 and 44 allows additional quantities of cold-water-soluble powder to be applied as relatively uniform layer 20 and 48 to the layer of water-based adhesive composition 18 and 44. In particular, use of the preferred mixture of super absorbent materials and standard gelling agents to form the cold-water-soluble powder provides a powder which hydrates rapidly, with a high absorbency potential, to form the reconstituted medium. This in turn provides culture media devices 10 and 30 which can accept larger volumes of aqueous test sample to form the reconstituted medium without the need to resort to spacer elements, side walls, sponges, filter paper, and the like.

Usefulness of the Invention

Use of culture media devices 10 and 30 of the present invention will be discussed with specific reference to the device of FIG. 1, although the same method of use would apply equally well to the device of FIG. 3. To use the device of FIG. 1 as a substitute for a standard, liquid media-filled pour plate, cover sheet 22 is pulled back and a predetermined quantity (e.g., 1 ml to 5 ml) of an aqueous test sample is placed on the layer of cold-water-soluble powder 20 coated on body member 11. The gelling agent quickly hydrates to form a reconstituted medium capable of supporting microorganism growth. Cover sheet 22 is then replaced over body member 11, and a weighted plate (not shown) is placed on top to completely spread the aqueous test sample and reconstituted medium. The device is then incubated for a predetermined period of time. Any colonies of microorganisms which grow in the medium can then be counted through transparent cover sheet 22, and/or body member 11.

Device 10 can also be conveniently used to test the surfaces of various objects to determine the extent of microbial contamination (i.e., "Rodac testing"). Specifically, cover sheet 22, coated only with a pressure-sensitive adhesive, is pulled back and touched to the surface being tested, thereby picking up any microorganisms present on the surface being tested. The cold-water-soluble powder of culture media device 10 is then hydrated to form the reconstituted medium, cover sheet 22 is replaced, and device 10 is incubated.

A further test for Staphylococcus bacteria can also be performed when using culture media devices 10 and 30 of the present invention. To test for Staphylococcus bacteria, the water-based adhesive composition incorporates a phosphatase-indicating dye, such as 5-bromoy-4-chloro-3-indolyl phosphate disodium salt. Upon inoculation of culture media device 10 with an aqueous test sample, any Staphylococcus bacteria present in the sample produce phosphatase, which then breaks down the selective dye to form blue-colored Staphylococcus colonies. However, some Streptococcus Group D bacteria also produce phosphatase. Therefore, an esculin-impregnated disc at a concentration of 5 mg of esculin per disc is placed onto the reconstituted medium after an initial incubation period of 48 hours at 37° C. The esculin (Sigma Chemical, Inc., St. Louis, Mo.) in the disc results in a brown precipitate forming around any Streptococcus Group D colonies growing on culture media device 10. Accordingly, Staphylococcus colonies can be identified and quantified on device 10, as the only blue-colored, non-precipitate-containing, microorganism colonies growing on the reconstituted medium of culture media device 10.

The invention will be further illustrated by reference to the following non-limiting Examples. All parts and percentages are expressed as parts by weight unless otherwise indicated.

COMPARATIVE EXAMPLES 1-6

EXAMPLES 7-12

Separate mixtures of 68.8 g IGEPAL TM CA-897 (nonionic surfactant) and 32 g N-vinylpyrrolidone (NVP) in 2400 g deionized water, and 2.4 g lauroyl peroxide in 1568 g isooctyl acrylate (IOA) were prepared, then mixed together in a Waring blender, and homogenized for one minute. The resulting homogenate was added to a nitrogen-purged 5-liter reaction flask equipped with a paddle stirrer, and heated with stirring to 60° C. The start of the polymerization reaction was signaled by heat liberation, which was allowed to progress to a peak temperature of about 90° C. The reaction was then allowed to cool to 70° C., and was held at that temperature, with stirring, for two hours. After cooling to room temperature, the reaction mixture was filtered through cheesecloth, Baird-Parker Nutrient formulation added, and the filtrate coated onto a suitable substrate. The resulting mixture comprised about 40% adhesive solids, with the remainder being water and displayed a particle size of about 0.3μ to about 0.8μ, a pH range of about 6 to about 8, a Brookfield viscosity of about 5 to about 15 cps. In addition, another water-based adhesive composition according to the present invention was made using the same procedure as described above, except acrylamide (ACM) monomer was substituted for the N-vinylpyrrolidone (NVP) monomer.

Table I below compares growth figures for several species of Staphylococcus bacteria on standard self-supporting substrates (with and without an air-permeable membrane) coated only with Baird-Parker Nutrient formulation (Acumedia, Inc., Baltimore, Md.), vs. substrates coated with a conventional water-based adhesives of isooctyl acrylate (IOA) and acrylic acid (AA) in a weight ratio of 95:5, prepared using an ionic emulsifier and an ionic initiator. The conventional IOA/AA adhesive incorporated Baird-Parker Nutrient formulation in a 1:1 (column 3, Table 1) and a 1:2 (column 4, Table 1) ratios by weight of adhesive to nutrient. As can be seen in Table I, the standard water-based adhesives completely suppressed the growth of the various strains and species of Staphylococcus bacteria. In contrast, the substrates coated only with nutrient, and no adhesive, show normal Staphylococcus colony growth patterns.

Table II below gives growth figures (i.e., the number of colonies counted) for the same species/strain of Staphylococcus bacteria as used in Comparative Examples 1-6 on a Control pour-plate filled with agar media and Standard Methods Nutrient formulation (Acumedia, Inc., Baltimore, Md.) (column 1); in the presence IGEPAL TM CA897 nonionIc emulsifier (2% solution) incorporated into the control pour-plate (column 2); and for the two formulations IOA and ACM, and IOA and NVP, at 98:2 weight ratios) of water-based adhesive compositions of the present invention coated onto self-supporting substrates (Columns 3 and 4). The growth results disclosed in Table II indicate that the water-based adhesive compositions of the present invention provide growth for Staphylococcus bacteria which is equivalent to, if not better than, the Control and IGEPAL TM pour-plates.

TABLE 1

Number of colonies counted of various species/strains of Staphylococcus bacteria grown on nutrient-coated substrates (with and without an air-permeable membrane) versus substrates coated with conventional water-based adhesive compositions incorporating nutrient therein.

| Comp. Ex. No. | Staph. Species/ Strain | Nutri. coated Subst. (mem) | Nutri. coated Subst. (no mem) | Conventional IOA/AA Adhesive (1:1) | Conventional IOA/AA Adhesive (1:2) |
|---|---|---|---|---|---|
| 1 | *S. intermedius* | 255 | 342 | 0 | 0 |
| 2 | *S. aureus/* Z288 | 418 | 479 | 0@ | 0@ |
| 3 | *S. aureus/* 6538 | 131 | 14 | 0 | 0 |
| 4 | *S. aureus/* fish | 381 | 342 | 0 | 0 |
| 5 | *S. aureus/* F265' | 140 | 110 | 0 | 0 |
| 6 | *S. aureus/* Fla. Halo | 269 | 186 | 0 | 0 |

@Approximately 400 microorganism colonies counted, but no blue colonies, indicating the presence of *Staphylococcus aureus*, Strain Z288, were recorded.

TABLE 2

Number of colonies counted of various species/strains of Staphylococcus bacteria grown on a control pour plate, the Control pour plate with IGEPAL TM nonionic emulsifying agent therein, and two formulations of the water-based adhesive compositions of the present invention.

| Ex. No. | Staph. Species/ Strain | Control Pour Plate | Pour Plate IGEPAL TM (2%) | New Adhesive Comp. (IOA/ACM) (98:2) | New Adhesive Comp. (IOA/NVP) (98:2) |
|---|---|---|---|---|---|
| 7 | *S. intermedius* | 450 | 430 | 650 | 560 |
| 8 | *S. aureus/* Z288 | 450 | 480 | 940 | 810 |
| 9 | *S. aureus/* 6538 | 120 | 90 | 195 | 195 |
| 10 | *S. aureus/* fish | 850 | 850 | 1300 | 1300 |
| 11 | *S. aureus/* F265 | 540 | 500 | 650 | 600 |
| 12 | *S. aureus/* Fla. Halo | 270 | 270 | 300 | 300 |

EXAMPLE 13

One side of 0.13 mm thick polyethylene-coated paper (Schoeller Paper Inc., of Pulaski, N.Y.) was knife-coated with a water-based adhesive composition at a level (measured when dried) of 6.2 mg/cm$^2$, and dried. The water-based adhesive composition was formed by dissolving 300 g of Violet Red Bile nutrient formulation (Acumedia Inc., Baltimore, Md.) (Table 3 below) and 2.5 g of guar gum (Hi-Tek Polymers Inc. of Louisville, Ky.), with stirring, in 1 liter of an emulsion suspension of a water-insoluble adhesive copolymer of isooctyl acrylate (IOA) and N-vinylpyrrolidone (NVP) at a 98:2 weight ratio (IOA:NVP). The components of the water-based adhesive composition included 1568 g of IOA (38.5 parts by weight), 32 g of NVP (0.8 parts), 2400 g of deionized water (59 parts), 68.8 g of IGEPAL TM CA897 nonionic surfactant (1.7 parts), and 24 g of lauroyl peroxide (0.06 parts by weight). Next, 0.01 g of crystal violet dye and 0.48 g of neutral red dye (Sigma Chemical, St. Louis, Mo.) were dissolved in 100 ml of methanol, and this solution was added with stirring to above solution. The combined solutions were allowed to stand overnight at a temperature of 4°–8° C., coated onto the substrate, and dried in an air oven at 93° C., to yield a sticky layer of the water-based adhesive composition on the surface of the substrate.

A mixture of cold-water-soluble powders, formed of equal proportions by weight of xanthan gum (Keltrol TM, Kelco Inc., San Diego, Calif.), locust bean gum (Myprodyne TM; Hi-Tek Polymers, Louisville, Ky.), Ucargel XLG-100 TM (Union Carbide, Boundbrook, N.J.), and Water Lock TM A-100 (Grain Processing Corp., Muscatine, Iowa), was dusted over the surface of the water-based adhesive layer. Any excess powder was shaken loose. This adhesive-coated and powder-coated paper was used to form the bottom portion of the culture media device.

A cover sheet was made from a sheet of 0.04 mm thick, transparent, biaxially-oriented, corona-treated polypropylene film, coated with a noninhibitory adhesive copolymer of isooctyl acrylate (IOA) and acrylamide (ACM) in a 98:2 weight ratio (IOA:ACM), at a level (measured when dry) of 0.93 mg/cm$^2$, and dried. The adhesive was then dusted uniformly with a mixture of xanthan gum (Keltrol TM), Locust bean gum (Myprodyne TM), Ucargel XLG-lOO TM and Water Lock TM A-100 in a 1:1:1:1 weight ratio. The excess powder was shaken loose.

Both the adhesive-coated and powder-coated bottom portion and cover sheet were cut into 10 cm × 10 cm pieces, placed together with the powdered sides facing each other, and heat-sealed together along one edge. The completed culture media device was enclosed in a foil package and sterilized with gamma radiation.

In use, the device was placed on a level surface, and the top cover sheet folded back, exposing the powder-coated surface of the bottom section of the device. A 5 ml aqueous test sample containing coliform bacteria was carefully placed in the center of the bottom section of the device, and the cover sheet replaced, powder-coated side down. A weighted spreader was applied to evenly spread the aqueous test sample over the powder-coated surfaces of the culture media device. The inoculated device was placed in an incubator and incubated in the normal manner. After incubation, the device was read just as with a standard pour-plate. The crystal violet and neutral red dye selective agents included in the nutrient formulation acted as selective agents, and were metabolized by the coliform bacteria, which were thereby dyed a red color for ease of quantification. In addition, the bile salts of the nutrient formulation also served as selective agents which inhibited the growth of gram-positive bacteria.

TABLE 3

Components of Violet Red Bile nutrient formulation as measured in grams/liter for culture media device of Example 13.

| Component | Weight g/l |
| --- | --- |
| yeast extract | 18 |
| pancreatic digest of gelatin | 39 |
| bile salts | 3 |
| lactose | 40 |
| sodium chloride | 10 |
| meat peptone | 3 |

Example 13 shows that a culture media device according to the present invention can be constructed and used to contain and grow gram negative bacteria using a 5 ml test sample. Previously, samples of this volume could not be contained without additional structures, such as side-walls, spacer elements, or absorbent elements. Furthermore, incorporation of selective agents, such as dyes and inhibitory salts, can be utilized to selectively grow desired bacteria species and/or help to visualize colonies of those species.

EXAMPLE 14

Culture media devices were made in the same manner as that described in Example 13, except that an Advent TM microporous membrane (3M, St. Paul, Minn.) was laminated to the upper surface of the polyethylene-coated paper substrate by a layer of an IOA:ACM adhesive copolymer (98:2 weight ratio) at a level (when measured dry) of 0.93 mg/cm$^2$. The total thickness of the two-layered body member of the microporous membrane and polyethylene-coated paper was 0.5 mm.

The top surface of the membrane was knife-coated with a water-based adhesive composition, and powder-coated as in Example 13, except that the nutrient composition included in the water-based adhesive composition included a Baird-Parker Broth formulation (Acumedia, Baltimore, Md.), the specific composition of which is given below in Table 4. In addition, 10.0 g/l of lithium chloride, 0.017 g/l of colistin methane sulfonate, and 0.026 g/l of nalidixic acid (available from Sigma Chemical, St. Louis, Mo.) as selective agents were added to the solution. In particular, each of these selective agents served to selectively inhibit the growth of non-Staphylococcus bacteria. Furthermore, 0.1 g/l of 5-bromo-4-chloro-3-indolyl phosphate dye (B-C-I phosphate) as a disodium salt was added to the composition to facilitate the visualization and counting of Staphylococcus colonies.

The cover sheet was fabricated according to the procedure of Example 13, and was cut into rectangular pieces of about 7.5 cm × 10 cm, along with the bottom portions of the culture media device, and both were then heat-sealed together along one edge, sterilized, and packaged to form the completed culture media devices.

In use, the culture media devices were inoculated by the procedure described in Example 13. However, Staphylococcus bacteria, instead of coliform bacteria, were used as the microbiological organism in the aqueous test sample. A total of 1 ml of test sample was placed on the powder-coated surface of the bottom portion of the devices. After inoculation, spreading, and incubation, the Staphylococcus bacteria were identified according to the usual procedure utilized with standard pour-plates, including the use of an esculin-impregnated disc to distinguish certain strains of Streptococcus Group D bacteria from the desired Staphylococcus bacteria.

TABLE 4

Components of Baird-Parker Broth nutrient formulation as measure in grams/liter for Example 14.

| Component | Weight g/l |
| --- | --- |
| beef extract | 5 |
| casein peptone | 10 |
| yeast extract | 1 |
| glycine | 12 |
| sodium pyruvate | 10 |
| mannitol | 5 |
| B-C-I phosphate | 0.1 |

Example 14 shows that the culture media device of the present invention can be made to contain and grow a 1 ml sample of Staphylococcus bacteria without resorting to side-walls, spacer elements, or absorbent elements, such as sponges or filter paper.

EXAMPLES 15-20

A culture media device in accordance with the present invention was constructed with the materials and according to the procedures disclosed in Example 13. The effectiveness of this device was compared with a standard Petrifilm TM Coliform Count Plate (3M, St. Paul, Minn.). The Example culture media device was inoculated with a 5 ml sample aqueous suspension of different species of coliform bacteria, while a 1 ml sample was used with the Petrifilm TM device. Each were incubated in accordance with standard procedures. The colonies were then counted. The comparative count results, shown below in Table 5 are expressed in terms of Colony Forming Units (CFU) per ml of inoculum.

TABLE 5

Comparative colony counts (CFU) of different species of coliform bacteria grown on a culture media device of the present invention and a prior art Petrifilm TM device.

| Example | Species of Coliform | Device of Ex. 13 | Petrifilm TM Device |
| --- | --- | --- | --- |
| 15 | Enterobacter cloace | 160 | 145 |
| 16 | Klebsiella oxytoca | 250 | 150 |
| 17 | Enterobacter cloace | 350 | 250 |
| 18 | coliform sp. | 36 | 43 |
| 19 | coliform sp. | 160 | 190 |
| 20 | Escherichia coli | 150 | 160 |

The comparative results from Examples 15 through 20 illustrate that the 5 ml culture media device in accordance with the present invention performs at least as well, and often better, for the enumeration of coliform bacteria than does the present 1 ml sample-size Petrifilm TM device.

EXAMPLES 21-30

A culture media device in accordance with the present invention was constructed with the materials and according to the procedures given in Example 14. The effectiveness of this device was compared with a standard Petri dish pour-plate using Baird-Parker agar medium (See Table 4). Both the Inventive culture media device and the comparative pour-plate were inoculated with 1 ml aqueous suspension of different strains of Staphylococcus aureus bacteria, and incubated in accordance with standard procedures. The colonies were then counted. The comparative count results, shown below in Table 6, are expressed in terms of Colony Forming Units (CFU) per ml of inoculum.

TABLE 6

Comparative colony counts (CFU) of different strains of Staphylococcus aureus bacteria grown on a culture media device of the present invention and a Petri dish.

| Example | Strain Number | Device of Example 14 | Petri Dish |
| --- | --- | --- | --- |
| 21 | 1043 | 336 | 275 |
| 22 | 1060 | 365 | 315 |
| 23 | 1068 | 275 | 300 |
| 24 | 1072 | 215 | 250 |
| 25 | 1078 | 135 | 120 |
| 26 | 1081 | 145 | 135 |
| 27 | 1112 | 290 | 345 |
| 28 | 1117 | 260 | 300 |
| 29 | 1119 | 330 | 390 |
| 30 | 1168 | 250 | 200 |

The comparative results from Examples 21-30 illustrate that the 1 ml culture media device in accordance with the present invention performs at least as well, and often better, for the enumeration of Staphylococcus aureus bacteria than do the more cumbersome Petri dish pour-plates.

While in accordance with the patent statutes, description of the preferred weight fractions, processing conditions, and product usages have been provided, the scope of the invention is not to be limited thereto or thereby. Various modifications and alterations of the present invention will be apparent to those skilled in the art without departing from the scope and spirit of the present invention. The Examples described in this application are illustrative of the possibilities of varying the size of the culture media devices, and the amounts and types of water-based adhesive compositions and nutrient formulations to achieve properties for specific purposes.

Consequently, for an understanding of the scope of the present invention, reference is made to the following claims.

What is claimed is:

1. A culture media device comprising:
   (a) a body member comprising a self-supporting substrate with upper and lower surfaces;
   (b) a layer of a water-based adhesive composition coated on the upper surface of the substrate, wherein the water-based adhesive composition comprises a water-insoluble adhesive, a non-inhibitory emulsifying agent, and at least one hydrophilic agent selected from the group consisting of a nutrient for growing microorganisms, a selective agent, and combinations thereof; and
   (c) cold-water-soluble powder comprising at least one gelling agent adhered uniformly to the layer of the water-based adhesive composition.

2. The culture media device according to claim 1, wherein the ratio of parts by weight of hydrophilic agent to total parts by weight of water-based adhesive composition is from about 2:3 to about 1:10.

3. The culture media device according to claim 1, wherein the ratio of parts by weight of hydrophilic agent to total parts by weight of water-based adhesive composition is from about 1:2 to about 1:4.

4. The culture media device according to claim 1, further comprising a cover sheet having inner and outer surfaces and covering at least a portion of the body member.

5. The culture media device according to claim 4, wherein the cover sheet is releasably adhered to at least a portion of the body member.

6. The culture media device according to claim 4, wherein the cover sheet comprises a transparent polymer film selected from the group consisting of a polyester film, a polyolefin film, a polystyrene film, and combinations thereof.

7. The culture media device according to claim 4, wherein the cover sheet further comprises a layer of noninhibitory adhesive coated on at least a portion of the inner surface of the cover sheet, and a layer of the cold-water-soluble powder uniformly adhered to the layer of noninhibitory adhesive.

8. The culture media device according to claim 1, wherein the substrate is substantially water-proof.

9. The culture media device according to claim 1, wherein the substrate comprises a polymer film selected from the group consisting of a polyester film, a polyolefin film, a polystyrene film, and combinations thereof.

10. The culture media device according to claim 1, wherein the body member further comprises an air-permeable membrane having top and bottom surfaces, the bottom surface of the air-permeable membrane being affixed to the upper surface of the substrate, and wherein the layer of the water-based adhesive composition is coated on the top surface of the air-permeable membrane.

11. The culture media device according to claim 10, wherein the bottom surface of the air-permeable membrane is affixed to the upper surface of the substrate by an adhesive.

12. The culture media device according to claim 10, wherein the air-permeable membrane comprises a polymer selected from the group consisting of polypropylene, polyethylene, polyethylene terephthalate, polybutylene terephthalate, nylon, polyvinylidine fluoride, and combinations thereof.

13. The culture media device according to claim 10, wherein the air-permeable membrane exhibits a Gurley porosity measurement of from about 10 to about 50 seconds.

14. The culture media device according to claim 1, wherein the cold-water-soluble powder comprises a mixture of a super absorbent material and a standard gelling agent.

15. The culture media device according to claim 14, wherein the standard gelling agent is selected from the group, consisting of xanthum gum, guar gum, locust bean gum, carboxymethyl cellulose, hydroxyethyl cellulose, algin, and combinations thereof.

16. The culture media device according to claim 14, wherein the super absorbent material is selected from the group consisting of glycol modified polysaccharides, starch-graft-poly(sodium acrylate-co-acrylamide), and combinations thereof.

17. The culture media device according to claim 14, wherein the cold-water-soluble powder comprises equal parts by weight of super absorbent material and standard gelling agent.

18. The culture media device according to claim 1, wherein the cold-water-soluble powder comprises a sufficient amount of the gelling agent to provide a gel when hydrated with a predetermined amount of an aqueous test sample.

19. The culture media device according to claim 18, wherein the cold-water-soluble powder forms from about a five percent to about a fifteen percent solution when the predetermined amount of the aqueous test sample is added thereto.

20. The culture media device according to claim 1, wherein the cold-water-soluble powder further comprises nutrient for growing microorganisms.

21. The culture media device according to claim 1, wherein the body member has a grid pattern printed thereon.

22. The culture media device according to claim 1, wherein the water-based adhesive composition is maintained at a pH of about 7.

23. The culture media device according to claim 1, wherein the water-insoluble adhesive is a pressure-sensitive adhesive.

24. The culture media device according to claim 24, wherein the pressure-sensitive adhesive is a copolymer of isooctyl acrylate and acrylamide, or a copolymer of isooctyl acrylate and N-vinylpyrrolidone.

25. The culture media device according to claim 24, wherein the weight ratio of isooctyl acrylate to acrylamide, and isooctyl acrylate to N-vinylpyrrolidone, is about 98:2.

26. The culture media device according to claim 1, wherein the noninhibitory emulsifying agent comprises a nonionic emulsifying agent.

27. The culture media device according to claim 26, wherein the nonionic emulsifying agent comprises octyl phenoxy poly(ethylene oxide) ethanol.

28. The culture media device according to claim 1, wherein the selective agent is selected from the group consisting of an antibiotic, a dye, an inhibitory salt, and combinations thereof.

29. The culture media device according to claim 28, wherein the selective agent is an antibiotic selected from the group consisting of colistin methane sulfonate, nalidixic acid, and combinations thereof.

30. The culture media device according to claim 28, wherein the selective agent is a dye which is metabolizable by microorganisms, and which causes the microorganisms grown on the culture media device to be colored or fluoresce.

31. The culture media device according to claim 30, wherein the dye is selected from the group consisting of triphenyltetrazolium chloride, p-tolyltetrazolium red, tetrazolium violet, veratryltetrazolium blue, neutral red, crystal violet, 5-bromo-4-chloro-3-indolyl phosphate, and combinations thereof.

32. A method of making a culture media device useful for growing microorganisms comprising:
(a) providing a body member comprising a self-supporting substrate with upper and lower surfaces, and a water-based adhesive composition comprising a water-insoluble adhesive, a noninhibitory emulsifying agent, water, and at least one hydrophilic agent selected from the group consisting of a nutrient for growing microorganisms, a selective agent, and combinations thereof;
(b) coating a layer of the water-based adhesive composition on the upper surface of the substrate; and,
(c) uniformly affixing cold-water-soluble powder comprising at least one gelling agent to the layer of the water-based adhesive composition.

33. The method according to claim 32, further comprising, prior to the affixing step, drying the layer of the water-based adhesive composition until substantially all of the water in the composition is removed.

34. The method according to claim 32, further comprising, covering at least a portion of the substrate with a cover sheet having inner and outer surfaces.

35. The method according to claim 32, further comprising, prior to the coating step, adhering an air-permeable membrane having top and bottom surfaces to the upper surface of the substrate, wherein the layer of the water-based adhesive composition is coated on the top surface of the air-permeable membrane.

36. A method of using a culture media device to detect microorganisms in an aqueous test sample comprising:
 (a) providing a culture media device comprising a body member including a self-supporting substrate with upper and lower surfaces, and a layer of a water-based adhesive composition coated on the upper surface of the substrate, wherein the water-based adhesive composition comprises a water-insoluble adhesive, a non-inhibitory emulsifying agent, and at least one hydrophilic agent selected from the group consisting of a nutrient for growing microorganisms, a selective agent, and combinations thereof, and wherein a uniform layer of a cold-water-soluble powder comprising at least one gelling agent is adhered to the layer of the water-based adhesive composition;
 (b) inoculating the culture media device with a predetermined volume of an aqueous test sample to form a reconstituted medium;
 (c) incubating the culture media device for a predetermined period of time; and,
 (d) counting the number of microorganism colonies growing on the reconstituted medium.

* * * * *

UNITED STATES PATENT AND TRADEMARK OFFICE
CERTIFICATE OF CORRECTION

PATENT NO. : 5,232,838
DATED : August 3, 1993
INVENTOR(S) : Robert L. Nelson, Michael D. Crandall, and Mary S. Ramos It is certified that error appears in the above-indentified patent and that said Letters Patent is hereby corrected as shown below:

Col. 7, line 37, "(20 thick" should read --(20 u thick--

Col. 14, line 53, "bromoy" should read --bromo--

Col. 17, line 18, "24" should read --2.4--

Col. 19, line 10, "measure" should read --measured--

Col. 22, line 18, "24" should read --23--

Signed and Sealed this

Twenty-fourth Day of May, 1994

Attest:

BRUCE LEHMAN

Attesting Officer

Commissioner of Patents and Trademarks